United States Patent [19]

Re et al.

[11] 4,133,807

[45] Jan. 9, 1979

[54] 4-THIOXO-2-AZETIDINONES

[75] Inventors: Luciano Re; Alberto Brant, both of Rome; Luciano Bassignani, Passo Corese (Rieti), all of Italy

[73] Assignee: Snamprogetti, S.p.A., Milan, Italy

[21] Appl. No.: 769,527

[22] Filed: Feb. 17, 1977

[30] Foreign Application Priority Data

Feb. 23, 1976 [IT] Italy .............................. 20457 A/76

[51] Int. Cl.$^2$ ................. C07D 205/10; C07D 205/08; C07D 513/04
[52] U.S. Cl. .......................... 260/239 A; 260/306.7 C; 204/158 R
[58] Field of Search .................. 260/239 A, 326 S

[56] References Cited

U.S. PATENT DOCUMENTS 3,974,154   8/1976   Naylor .............................. 260/239 A

*Primary Examiner*—Donald G. Daus
*Assistant Examiner*—Mark L. Berch
*Attorney, Agent, or Firm*—Morgan, Finnegan, Pine, Foley & Lee

[57] ABSTRACT

A method is disclosed for the preparation of a class of dehydropenicillins by irradiating substituted 4-acyl-methylthio-2-azetidinones and subsequently subjecting the as-obtained product to cyclization. Processing conditions and analytical data are reported.

6 Claims, No Drawings

4-THIOXO-2-AZETIDINONES

This invention relates to 5,6-dehydropenicillins ("dehydropenicillins") and to a method for their preparation.

Dehydropenicillins are a novel class of penicillin derivatives which are characterized by the presence of an unsaturation in the beta-lactamic ring structure and which belong to the class of the 2-azetine-4-ones of which only a few members were known heretofore no one of which was bicyclic.

The structure of the dehydropenicillins is illustrated by the general formula:

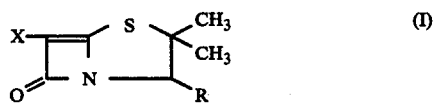

in which X is an aminic group, also monosubstituted or disubstituted whereas R is a carboxyl group or a salt, an amide, an ester or a thioester thereof.

Specifically, the group R can be a carboxylic ester or thioester of an alkyl (for example methyl, ethyl, propyl, butyl), of an aralkyl (for example benzyl or substituted benzyl), of an aryl (for example phenyl or substituted phenyl) or a 2,2,2-trichloroethyl ester or thioester of a carboxylic acid.

The selection of an ester the cleavage of which is carried out under bland conditions (for example a benzyl ester or a 2,2,2-trichloroethyl ester) should be preferred in the case in which it is desired to prepare from esters of the general formula (I) the corresponding free carboxylic acids from which, in their turn, it is possible to prepare other carboxyl derivatives with procedures which are within the purview of anyone skilled in the art.

Specifically, the group R can also be a mono- or dialkyl (such as mono- or diethylamide), mono- or diaralkyl (for example mono- or dibenzylamide), or mono- or diaryl (such as mono- or diphenylamide) carboxylamide.

Both the basic salts to the carboxyl group and the acidic salts to the aminic group of the dehydropenicillins of the general formula (I) can be prepared with methods known to anyone skilled in the art from the corresponding precursors.

In the general formula (I) particular examples of substituted aminic groups such as X are aralkylaminic groups (such as benzylamino, triphenylmethylamino), or acylaminic groups (such as those present in natural penicillins or cephalosporins, such as phenylacetamido or phenoxyacetamido).

A particular example of the aminic group X (disubstituted) is represented by the phthalimido group.

According to the present invention, the preparation of such compounds is carried out, as shown in the pattern I, by irradiation of substituted 4-acylmethylthio-2-azetidinones of the type II or IIa to give, through a photochemical reaction of the Norris II type, the corresponding 4-thioxo-2-azetidinone derivative of the kind III or IIIa which, by subsequent basic treatment (in the case of III also acidic or merely a heat-treatment) gives rise to the formation of the dehydropenicillin I.

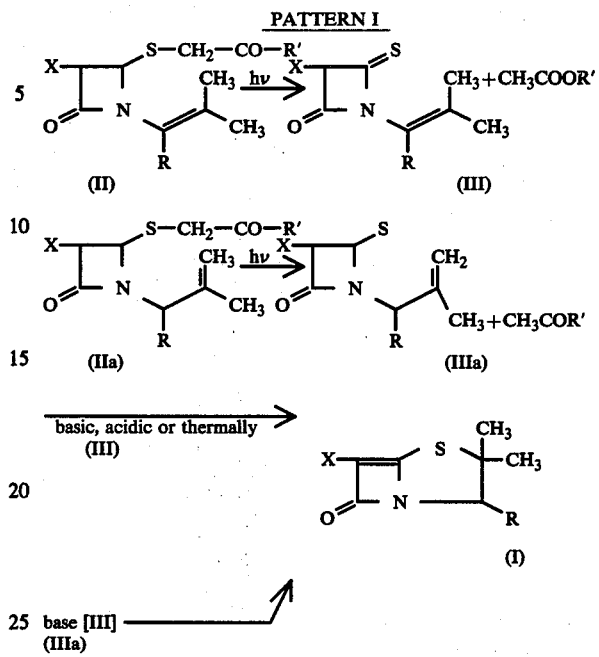

In the above reported pattern I, X and R have the same meaning as reported above and R' is an alkyl, aryl or aralkyl radical.

It should be noted that in the synthesis shown in the pattern I the nature of the groups X, or R of the starting compound II or IIa must not necessarily be that of the final product I as expected, inasmuch as it is also possible to effect, with conventional methods, a modification of such groups at the level of the intermediate III or IIIa, or after the cyclization of such intermediate to I.

It is to be noted, moreover, that for such a synthesis, it is possible to use starting compounds II or IIa, both in the cis or the trans form relative to the substituents on the $C_3$ and the $C_4$ of the lactamic ring.

The derivatives I such as obtained with the method shown in the pattern I are optically inactive chiral products which can be split into their enantiomers by conventional procedures as known to anyone skilled in the art.

An interesting aspect of the method according to the present invention, of which it is otherwise an integral part, is the fact that the precursors of the dehydropenicillins, compounds III and IIIa of the pattern I, are novel products: as a matter of fact no example of any 4-thioxo-2-azetidinone has been reported by the literature.

The starting compounds II and IIa of this synthesis are, on the contrary, a class of known products and can be prepared starting from derivatives of natural penicillins or by total synthesis, more detailedly:

(a) The compounds II in which X, R and R' have the same meaning as indicated above, from derivatives of penicillins, according to the German Offeleg. 2,204,105 and 2,254,632, or by total synthesis according to Lattrel, R., Liebigs Ann, Chem. 1974, 1361 and references cited therein;

(b) the compounds II or IIa in which X is a mono- or diacylamino group, R is an ester and R' as above, from penicillins according to Yashimoto M., et al., Tetrahedron Letters, 1972, 4387, or from penicillin sulphoxides according to German Offenleg. 2,138,320 or Lattrel R., Liebigs Ann. Chem. 1974, 1937;

(c) the compounds IIa carrying the other X and R groups and in which R' is as above, from the abovementioned derivatives in which X is a mono- or diacylamino group, R is an ester and R' is as above, using chemical and/or enzymatic procedures as known to anyone skilled in the art.

Lastly, the compounds II in which R' is an aryl, X is an R"NH group (in which R" is an aralkyl) and R a COOR''' group (wherein R''' is an alkyl, an aralkyl or an aryl) (V) can also be prepared with an original method which must thus also be considered as an integral part of the present invention, and is more direct than those indicated above, such method being shown in the pattern II (wherein Y = halogen and Ar= aryl), by reacting 6-aralkyl-aminopenicillates (IV, wherein R" and R''' have the same meanings given above) with halomethyl aryl ketones in the presence of a strong base.

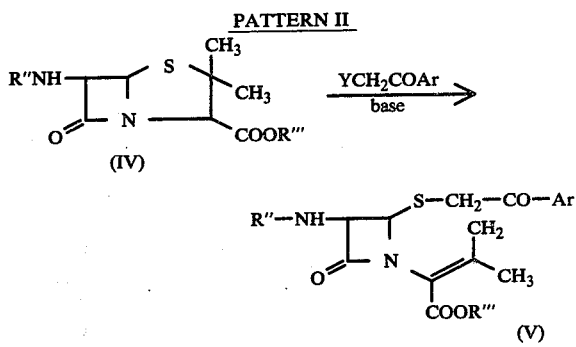

Also from the compounds V, with conventional procedures known to anyone skilled in the art, it is possible to prepare, in their turn, the other derivatives II with R'= aryl as already cited above.

More exactly, for the preparation of the dehydropenicillins I according to the present invention, the starting product II or IIa is subjected to the irradiation of an ultraviolet lamp, preferably of the kind with an average mercury pressure and equipped with a filter, preferably a Pyrex or Corex filter.

The reaction is carried out in an atmosphere of an inert gas (for example nitrogen) in an inert solvent (such as an aromatic solvent or in acetonitrile), anhydrous and oxygen-free and at a temperature in the range from −10° C. and +40° C. (preferably at room temperature) to give the derivative III or IIIa with generally high yields.

The intermediate III or IIIa is then treated in an anhydrous inert solvent (such as a halogen-aliphatic solvent or an aromatic solvent) with a quantity which can also be catalytic (when III or IIIa is a neutral molecule) of an organic base (preferably triethylamine) at a temperature in the range from −10° C. to +40° C. (preferably at room temperature) to give, with generally high yields, the dehydropenicillin I.

As an alternative, the cyclization of III to I can be carried out in an inert anhydrous solvent (such as an aliphatic or aromatic solvent), also with a Brønsted or a Lewis acid, preferably silica gel, or in a neutral environment by merely heating to a temperature between 50° C. and 150° C.

More detailedly, as regards the preparation of the starting products of the kind V according to the method of the present invention, the compound IV is reacted with a halomethyl aryl ketone (preferably bromo- or iodomethyl aryl ketone) in an inert anhydrous solvent (such as dimethylformamide, dimethylsulfoxide, tetrahydrofuran or mixtures of the latter with ter-butyl alcohol, but preferably with tetrahydrofuran alone) in the presence of a strong base which is capable of cleaving the thiazolidine ring of IV but incapable of cleaving the lactam ring of IV or V (such as an alkali metal hydride such as sodium hydride, or the alkali metal salt of a tertiary alcohol, preferably potassium ter-butylate), at a temperature comprised between −80° C. and +30° C. (preferably at −40° C.).

Derivatives of the type IV which are particularly suitable as the starting compounds for the preparation of the compounds V according to the pattern II are those in which R" is a triphenylmethyl group and this both from the point of view of the yield of the reaction as itself and the ease with which such a group can be removed from the product V to give the free amine from which it is possible to prepare, according to the conventional procedures, other aminic derivatives.

The importance of the dehydropenicillins I and of the 4-thioxo-2-azetidinones III and IIIa which are the subject-matter of the present invention lies in that these compounds are useful intermediates for the preparation of other derivatives of the penicillins and cephalosporins having a pharmaceutical interest.

In addition, a few of the dehydropenicillins I are endowed with a bland antibacterial activity.

The present invention is illustrated by the following examples which are not to be construed in any wise as limitation to the invention itself.

EXAMPLE 1

Preparation of the cis-1-(1-methoxycarbonyl-2-methyl-1-propenyl-3-triphenylmethylamino-4-phenacylthio-2-azetidinone(VII)

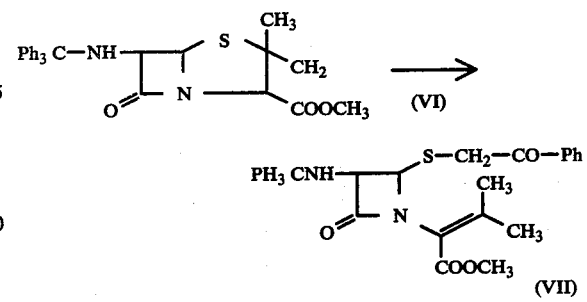

To a solution of 3.78 grams (8 millimols) of methyl-6beta-triphenylmethylaminopenicillanate (VI) and 1.75 grams (8 millimols) of phenacylbromide in 30 mls of anhydrous tetrahydrofuran are added during 30 mins. with stirring, in a nitrogen atmosphere and at a temperature of −40° C., 0.898 grams (8 millimols) of potassium ter-butylate dissolved in 40 mls of anhydrous tetrahydrofuran.

On completion of the addition, the mixture is stirred during 5 additional hours at the same temperature, then, still under nitrogen, neutralization is effected with a few drops of glacial acetic acid diluted in anhydrous tetrahydrofuran, filtration is carried out and the filtrate is evaporated under vacuum.

The thus-obtained residue is chromatographed on a silica-gel column (3 × 60 cm) eluting with benzene which contains 5% of ethyl acetate.

From the first eluates are isolated 1.71 grams of the starting compound (VI) which did not react (recovery 45.2%) and from the subsequent 1.52 grams of the pure product (yield 58.7% relative to the converted VI) in the form of a white foam.

I R (CHCl$_3$) : $\nu$max 3340 (NH), 3040 and 3020 (phenyls), 1760 (CO of the beta-lactam), 1720 (CO of the ester), 1673 (CO of the phenacyl), 1625 (C = C), 1595, 1580 and 1495 cm$^{-1}$ (phenyls).

NMR (CDCl$_3$) : $\delta$1.83 (3H,s) and 2.03 (3H,s)[(CH$_3$)$_2$C = C], 3.00 (1H,d, J = 8Hz, NH), 3.42 (2H,q, J = 14Hz, SCH$_2$), 3.80 (3H,s,COOCH$_3$), 4.60 (1H,q, J = 4 and 8Hz, 3-H), 4.92 (1H,d, J = 4Hz, 4-H), 6.90–7.90 (20 H,m,aromatics).

Mass spectrum: m/e 590, 485, 347, 243, 228, 155, 105, 77, 68.

Analysis for C$_{36}$H$_{34}$N$_2$O$_4$S: Calcd. C% = 73.19; H% = 5.80; N% = 4.74. Found C% = 72.80; H% = 6.02; N% = 4.91.

EXAMPLE 2

Preparation of the cis-1-(1-methoxycarbonyl-2-methyl-1-propenyl)-3-amino-4-phenacylthio-2-azetidinone hydrochloride (VIII).

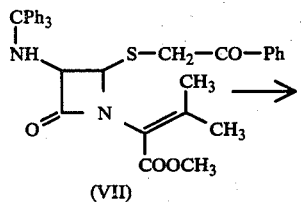
(VII)

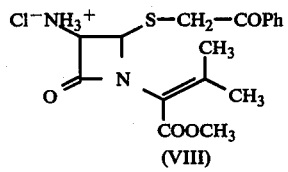
(VIII)

To 0.673 gram (1.14 millimol) of the product VII, prepared according to EXAMPLE 1, dissolved in 10 mls of anhydrous methylene chloride are added at −20° C. with stirring and in an anhydrous atmosphere (nitrogen), 7.0 mls of a 0.326-normal solution (2 equivalents) of gaseous hydrogen chloride in anhydrous methylene chloride.

The solution is stirred during 2 hours at the same temperature under nitrogen, then evaporated to dryness under vacuum and the gummy residue is taken up with a few mls of a mixture of ethyl ether and petroleum ether (anhydrous).

The precipitate is collected by filtration under nitrogen and dried in a vacuo to give 0.390 gram of the hydrochloride VIII (yield 89%) as a white solid which is very hygroscopic, and is sufficiently pure to be used in the following reaction (EXAMPLE 3) and for being spectrophotometrically identified.

I R (CHCl$_3$) : $\nu$ max 3060 and 3020 (phenyl), 1775 (CO of the beta-lactam), 1720 (CO of the ester), 1675 (CO of the phenacyl), 1620 (C = C), 1595, 1580 and 1490 cm$^{-1}$ (phenyl).

NMR (CDCl$_3$): $\delta$2.05 (3H,s) and 2.22 (3H,s) [(CH$_3$)$_2$C = C], 3.80 (3H,s,COOCH$_3$), 4.23 (2Hs,SCH$_2$), 5.87 (1H, d wide band, 4-H), 6.40 (1H,m wide band,3H), 7.00–7.90 (5H,m, aromatics), 8.35 (3H, wide band,NH$^+$$_3$).

EXAMPLE 3

Preparation of the cis-1-(1-methoxycarbonyl-2-methyl-1-propenyl-3-acetamido-4-phenacylthio-2-azetidinone (X)

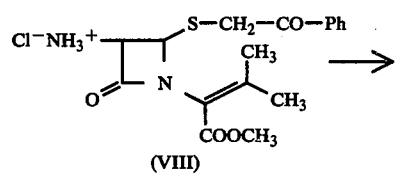
(VIII)

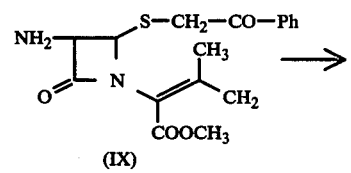
(IX)

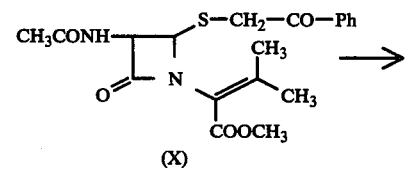
(X)

To 0.385 gram (1 millimol) of the hydrochloride VIII, prepared according to EXAMPLE 2, dissolved in 5 mls of anhydrous methylene chloride are added at 0° C. with stirring and in an anhydrous atmosphere (nitrogen), 140 microliters (millimol) of triethylamine.

After 30 mins. the mixture which contains the free amine IX is further cooled to −20° C. and are added, still with stirring and in a nitrogen atmosphere, 140 additional microliters of triethylamine followed by 71 microliters (1 millimol) of acetyl chloride dissolved in 2 mls of anhydrous methylene chloride and stirring is applied, then, for a few hours at 0° C.

Upon dilution with 10 additional mls of methylene chloride, the mixture is washed with water to neutrality and the organic phase, dried over sodium sulfate is evaporated to dryness in a vacuo.

The raw product is purified by chromatography on a thin preparative layer of silica gel, eluting then with ethyl ether-ethyl acetate (2 : 1) and extracting the product from the silica with chloroform.

There is obtained 0.085 gram of the product X, pure (yield 22%) in the form of a white foam.

I R (film): $\nu$ max 3320 (NH), 3050 and 3020 (phenyl), 1760 (CO of the beta-lactam, 1720 (CO of the ester), 1682 (shoulder, CO of the acetamide), 1673 (CO of the phenacyl), 1625 (C = C), 1595 and 1585 (phenyl), 1523 (NH), 1500 cm$^{-1}$ (phenyl).

NMR(CDCl$_3$): $\delta$ 1.86 (3H,s) and 2.13 (3H,s) [(CH$_3$)$_2$C = C], 1.93 (3H,s, CH$_3$CO), 3.75 (3H,s,COOCH$_3$), 3.80 (2H,s, SCH$_2$), 5.25 (1H,q, J = 8 and 4 Hz, 3-H), 5.40 (1H,d, J = 4Hz, 4-H), 7.10-8.00 (6H, aromatics and NH).

Mass spectrum: m/e 390, 291, 271, 239, 105, 84, 77,68.

EXAMPLE 4

Preparation of the 1-(1-methoxycarbonyl-2-methyl)1-propenyl)-3-phenoxyacetamido-4-thioxo-2-azetidinone (XII)

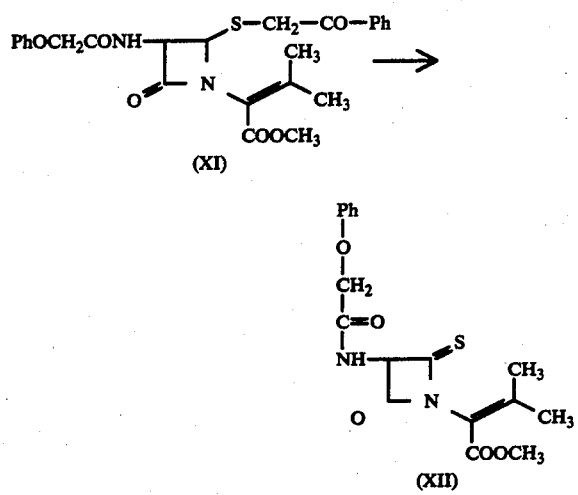

In a convention apparatus for photometric reactions with an immersion lamp having a cooling jacket of quartz and water jacket, equipped with a magnetic stirrer, capillary tube for nitrogen dipping to the bottom and outlet placed laterally and connected to a mercury layer, is charged under nitrogen 0.965 gram (2 millimols) of the product XI dissolved in 150 mls of anhydrous and degasified acetonitrile.

Purging is effected during 5 mins. in nitrogen stream, then irradiation is made at room temperature and with stirring during 45 mins. with a Hanovia lamp at average pressure of mercury, 500 Watts power, and with a Pyrex glass filter.

The solution is then transferred into a flask and, at room temperature, the solvent is first evaporated off under a vacuum of 13 mmHg and then the predominant fraction of the as-formed acetophenone with a vacuum of 0.1 mmHg during a few hours. The glassy residue of 0.645 gram (yield 89%) is formed nearly exclusively by the product XII and contains traces of acetophenone and very little (10% approx.) of the starting compound, XI. The product as obtained, which cannot be crystallized and is chromatographically unstable, is pure enough for the next reaction (EXAMPLE 9) and for being chromatographically identified.

I R (CHCl$_3$): ν max 3340 (NH), 3060 and 3040 (shoulder, phenyl), 1820 (CO of the beta-lactam); 1720 (CO of the ester), 1682 (CO of the phenoxyacetamide), 1635 (shoulder, C = C), 1595 and 1580 (shoulder, phenyl), 1528 (NH), 1490 cm$^{-1}$ (phenyl).

NMR (CDCl$_3$): δ 2.06 (3H,s) and 2.28 (3H,s) [(CH$_3$)$_2$ C = C], 3.80 (3H,s,COOCH$_3$), 4.36 (2H,s,OCH$_2$CO), 4.91 (1H,s, J = 8Hz, 3-H), 6.60–7.60 (5H,m, aromatics), 7.94 (1H,d, J = 8Hz, NH).

EXAMPLE 5

Preparation of the 1-(1-benzyloxycarbonyl-2-methyl-1-propenyl)-3-phenoxyacetamide-4-thioxo-2-azetidinone (XIV)

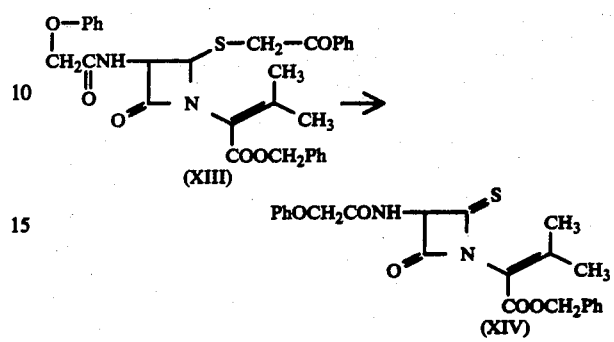

The procedure is similar to that disclosed in EXAMPLE 4 for the preparation of XII starting from XI, the initial starting compound being the benzyl ester XIII.

The as-obtained product XIV (yield 86%) in the form of a glassy solid, is sufficiently pure for the subsequent reaction (Example 10) and for being spectrophotometrically identified.

I R : similar to that of XII.

NMR (CDCl$_3$) : δ 2.06 (3H,s) and 2.28 (3H,s) (CH$_3$)$_2$ C = C, 4.36 (2H,s,OCH$_2$CO), 4.91 (1H,d, J = 8Hz,3-H), 5.17 (2H,s,COOCH$_2$), 6.60–7.60 (10H,m,aromatics), 7.94 (1H,d, J = 8Hz, NH).

EXAMPLE 6

Preparation of the 1-(1-methoxycarbonyl-2-methyl-1-propenyl)-3-triphenylmethylamino-4-thioxo-2-azetidinone (XV).

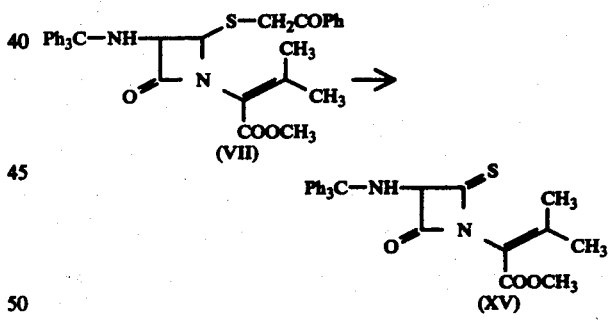

The procedure is similar to the disclosed in EXAMPLE 4 for the preparation of XII from XI, starting from the product VII prepared according to EXAMPLE 1.

The thus-obtained product XV (yield 81%) in the form of a homogeneous foam is sufficiently pure for the next reaction (EXAMPLE 11) but can be purified again, with low yields, by chromatography on a preparatory thin layer of silica gel eluting with benzene which contains 5% of ethyl acetate and extracting from the silica with chloroform the pure product in the form of a white foam.

I R (CHC1$_3$) : ν max 3330 (NH), 3050 and 3020 (phenyls), 1810 (CO of the beta-lactam), 1720 (CO of the ester), 1620 (shoulder, C = C), 1595, 1590 and 1490 cm$^{-1}$ (phenyls).

NMR (CDCl$_3$) : δ 1.81 (3H,s) and 2.26 (3H,s), (CH$_3$)$_2$ C = C, 2.80 (1H,d, J = 8Hz, NH), 3.67

(3H,s,COOCH₃), 4.75 (1H,d, J = 8Hz, 3-H), 7.10–7.70 (15H,m, aromatics).

Rotatory power: [α]$_D^{25}$ −1.4 (C = 1.00, CHCl₃).

EXAMPLE 7

Preparation of the 1-(1-methoxycarbonyl-2-methyl-1-propenyl)-3-acetamido-4-thioxo-2-azetidinone (XVI)

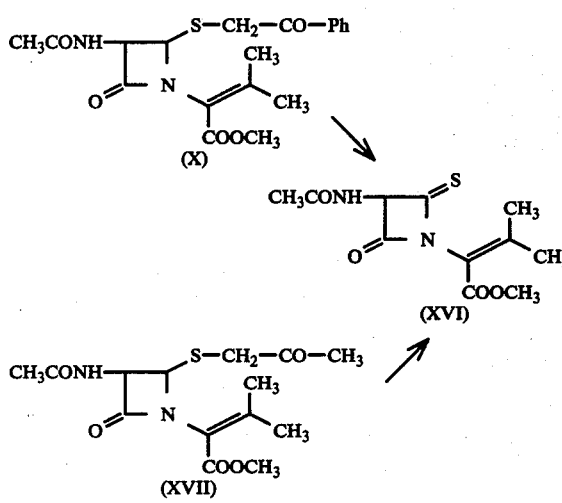

(a) The procedure is similar to that disclosed in Example 4 for the preparation of XII from XI, starting from the product X as prepared according to EXAMPLE 3.

The thus-obtained product XVI (yield 84.5%) in the form of a glassy solid is sufficiently pure for the next reaction (EXAMPLE 12a) and for being spectrophotometrically identified.

I R (CHCl₃): ν max 3320 (NH), 1820 (CO of the beta-lactam), 1722 (CO of the ester), 1675 (CO of the acetamide, 1635 (C = C), 1530 cm⁻¹ (NH).

NMR (CDCl₃): δ 2.00 (3H,s) and 2.32 (3H,s) [(CH₃)₂C = C], 2.08 (3H,s,CH₃CO), 3.73 (3H,s,COOCH₃), 4.93 (1H,d, J = 8Hz, 3-H), 7.53 (1H,d, J = 8Hz, NH).

(b) The procedure is similar to that disclosed in EXAMPLE 4 for the preparation of XII from XI, starting from the product XVII by using, instead, a filter of Corex glass and irradiating for 4 hours. In addition, at the end of the reaction, the evaporation at 0.1 mmHg is not required since, in this case, the as-formed ketone is acetone rather than acetophenone.

The gummy raw-product which is obtained, cannot be crystallized and is unstable to chromatography and is conveniently used as such for the next reaction (EXAMPLE 12a).

From the IR and NMR spectra it can be seen that the raw product contains about 40% of the product XVI and that the yield referred to the pure product is about 37%.

From a partial purification test of the raw material by repeated solubilizations in ethyl ether and precipitations with petroleum ether there is obtained, with very low yields, a gummy product which is purer and the IR and NMR spectra of which compared with those of the product obtained from X confirm the structure XVI.

EXAMPLE 8

Preparation of the 1-(1-methoxycarbonyl-2-methyl-2-propenyl)-3-acetamido-4-thioxo-2-azetidinone (XIX)

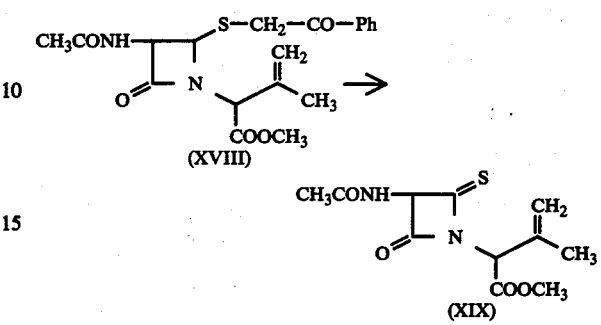

The procedure is similar to that disclosed in EXAMPLE 4 for the preparation of XII from XI, starting from the product XVIII. The product XIX which is obtained (yield 78.5%) as a glassy solid is sufficiently pure for the next reaction and for being identified spectrophotometrically.

I R (film): ν max 3300 (NH), 1818 (CO of the beta-lactam), 1740 (CO of the ester), 1670 (CO of the acetamide), 1530 cm⁻¹ (NH).

NMR (CDCl₃) δ 1.88 (3H,s, CH₃-C = C),2.07 (3H,s,CH₃CO—), 3.80 (3H,s,COOCH₃) 4.90–5.25 (4H,m,CH₂= C, 3-H and CHCOO), 7.50 (1H,d, J = 8Hz, NH).

EXAMPLE 9

Preparation of the methyl-6-phenoxyacetamidodehydropenicillanate (XX)

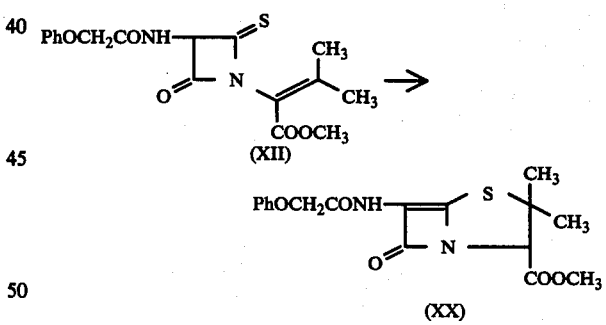

(a) To 0.645 gram (1.78 millimol) of the product XII, prepared according to EXAMPLE 4, dissolved in 30 mls of methylene chloride are added 0.08 ml of triethylamine and the solution stirred at room temperature in an anhydrous atmosphere (nitrogen) until observing at the IR the total discharge from the solution of the band at 1820 cm⁻¹ which is typical of the starting product XII (about 4 hours). The mixture is then dried in a vacuo and the raw product is purified by chromatography on a silica-gel column (2 × 20 cm) eluting with benzene and ethyl acetate (4 : 1). After the elution of a few impurities, there are isolated from the successive eluates 0.460 grams of the product XX (yield 71% from XII and 63.5% from XI) and then 0.05 gram approx. of the starting product XI of the previous reaction (EXAMPLE 4).

The dehydropenicillin XX is obtained as an amorphous white solid which is pure at the chromatography on thin layer and can be crystallized from ethyl ether-petroleum ether, m.p. 138° C.-139° C.

UV (EtOH): λ max (log E) 220 (3.88, 245 (3.87) and 328 millimicrons (4.41).

IR (CHCl$_3$) : ν max 3300(NH), 3060 and 3020 (phenyl), 1742 (CO of the ester), 1720 (CO of the beta-lactam), 1630 (CO of the phenoxyacetamide), 1595 and 1585 (shoulder, phenyl), 1565 (NH) 1493 cm$^{-1}$ (phenyl).

NMR (CDCl$_3$): δ 1.47 (3H,s) and 1.73 (3H,s) [(CH$_3$)$_2$C], 3.80 (3H,s,COOCH$_3$) 4.52 (1H,s,3-4), 4.80 (2H, s,OCH$_2$CO), 6.80-7.50 (5H, aromatics), 7.85 (1H,s,wide band, NH).

Mass spectrum : m/e 362, 269, 209, 199, 167, 139, 94, 66.

Analysis for C$_{17}$H$_{18}$N$_2$O$_5$S : Calcd. C % = 56.34; H% = 5.01; N % = 7.73. Found C% = 55.92; H % = 4.88; N % = 7.52.

(b) To 0.100 gram (0.28 millimol) of the product XII, prepared according to EXAMPLE 4, dissolved in 10 mls of chloroform are added 5 grams of silica gel. The slurry is stirred at room temperature overnight, then filtered, washing the silica repeatedly with chloroform.

The filtrate, evaporated in dryness in a vacuo shows at the IR the discharge of the band at 1820 cm$^{-1}$. The raw product is purified by chromatography on a preparative thin layer of silica gel eluting with benzene and ethyl acetate (7:3) and extracting the product from the silica with chloroform. There is obtained 0.038 gram of the product XX, identical to that obtained under (a).

Yield 38% from XII and 34% from XI.

(c) A solution in 10 mls of tetrachloroethylene of 0.100 gram (0.28 millimol) of the product XII, prepared according to EXAMPLE 4, is stirred for 10 hours at 90° C.-100° C. The cooled solution shows at the IR the discharge of the band at 1820 cm$^{-1}$ and is dried in vacuo and the residue purified as under (b). There is obtained 0.036 gram of the product XX, identical to that obtained under (a).

Yield 36 % from XII and 32 % from XI.

EXAMPLE 10

Preparation of the benzyl-6-phenoxyacetamidodehydropenicillanate (XXI)

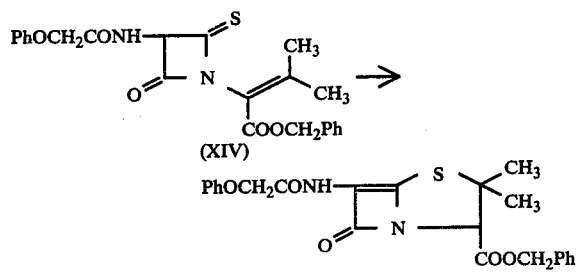

The procedure is similar to that described in EXAMPLE 9(a) for the preparation of XX from XII with triethylamine, starting from the benzyl ester XIV prepared according to EXAMPLE 5. The product XXI which is obtained (yield 72.5%) as a white amorphous solid, pure at the thin layer chromatography, can be crystallized from ethyl ether-petroleum ether, m.p. 129° C.−131° C.

IR (CHCl$_3$) : ν max 3300 (NH), 3040 and 3020 (phenyls), 1745 (CO of the ester), 1720 (CO of the be-talactam), 1630 (CO of the phenoxy-acetamide), 1600 and 1590 (shoulder, phenyls), 1565 (NH), 1495 cm$^{-1}$ (phenyls).

NMR (CDCl$_3$): δ 1.35 (3H,s) and 1.63 (3H,s) [(CH$_3$)$_2$C], 4.50 (H,s,3-4), 4.80 (2H,s, OCH$_2$CO), 5.18 (2H,s,COOCH$_2$), 6.70-7.50 (10H,m,aromatics), 7.85 (1H, s, wide band, NH). Mass spectrum : m/e 439, 438, 345, 303, 209, 94, 91, 66.

Analysis for C$_{23}$H$_{22}$N$_2$O$_5$S: Calcd. C % = 63.00; H % = 5.05; N % = 6.39. Found C % = 62.58; H % = 5.06; N % = 6.17.

EXAMPLE 11

Preparation of the methyl-6-triphenylmethylaminodehydropenicillanate (XXII)

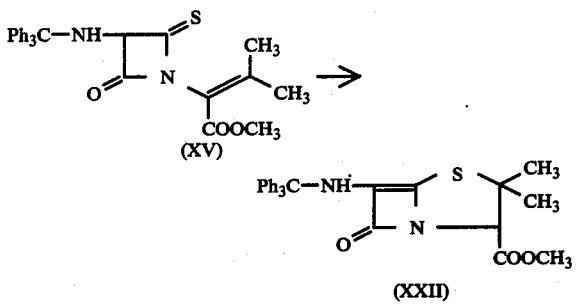

The procedure is similar to that disclosed in EXAMPLE 9 (a) for the preparation of XX from XII with triethylamine, starting from the product XV prepared according to the EXAMPLE 6.

In such case, however, to observe at the IR the discharge of the band at 1810 cm$^{-1}$ longer times are required (about 24 hours) and the thus-obtained raw material is purified on neutral alumina, eluting with benzene. The product which is now obtained (yield 23%) in the form of a foam is pure at the chromatography on thin layer, but it is poorly stable.

IR (CHCl$_3$): ν max 3320 (NH), 3060 and 3020 (phenyls), 1750 (CO of the ester), 1730 (CO of the betalactam), 1595, 1580 (shoulder), and 1490 cm$^{-1}$ (phenyls).

NMR (CDCl$_3$): δ 1.35 (3H,s), and 1.72 (3H,s) [(CH$_3$)$_2$C], 3.20 (1H,s, wide band, NH), 3.80 (3H,s,COOCH$_3$), 4.58 (1H, s, 3-4), 7.10-7.68 (15H,m,aromatics).

Analysis for C$_{28}$H$_{26}$N$_2$O$_3$S : Calcd. C % = 71.47; H % = 5.57; N % = 5.95. Found C % = 71.01; H % = 5.55; N % = 5.75.

EXAMPLE 12

Preparation of the methyl-6-acetamidodehydropenicillanate (XXIII)

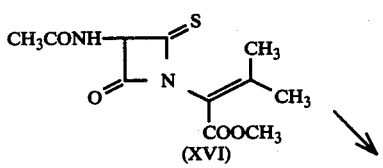

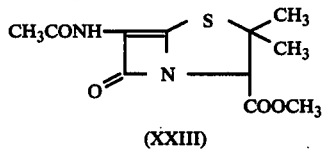

(XXIII)

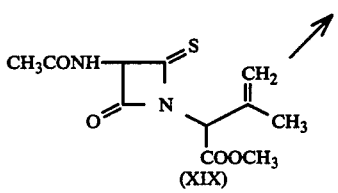

(XIX)

(a) The procedure is similar to that disclosed in EXAMPLE 9 (a) for the preparation of XX from XII with triethylamine, starting from the product XVI prepared according to EXAMPLE 7 (a) or 7 (b). The product which is obtained is purified in the first case by chromatography on column as described in EXAMPLE 9(a) and eluting, however, with ethyl ether-ethyl acetate (2:1) (yield 50.5% from XVI and 43% from X) and, in the second case by chromatography of preparatory thin layer of silica gel but eluting with ethyl ether-ethyl acetate (3:1) and extracting from the silica with chloroform (yield 24% from XVII). The product which is obtained as a glassy solid in both cases is pure and can be crystallized from ethyl ether-petroleum ether, m.p. 98° C.-100° C.

I R (CHCl$_3$): $\nu$ max 3300 (NH), 1740 (CO of the ester), 1715 (CO of the beta-lactam), 1630 (CO of the acetamide), 1570 cm$^{-1}$ (NH).

(NMR (CDCl$_3$): δ 1.47 (3H,s) and 1.75 (3H,s) (CH$_3$)$_2$C, 2.20 (3H,s,CH$_3$CO), 3.80 (3H,s,COOCH$_3$), 4.48 (1H,s,3-4), 7.60 (1H,s,COOCH$_3$), 4.48 (1H,s,3-4), 7.60 (1H, s, wide band, NH).

Mass spectrum : m/e 270, 238, 211, 199, 167, 139, 98, 39.

Analysis for C$_{11}$H$_{14}$N$_2$O$_4$S: Calcd. C % = 48.88; H % = 5.22; N % = 10.36. Found C % = 48.55; H % = 5.48; N % = 9.88.

(b) The procedure is similar to that in EXAMPLE 9 (a) for the preparation of XX from XII with triethylamine, starting from the product XIX prepared according to Example 8. The product which is obtained (yield 32% from( XIX and 25% from XVIII) as an amorphous solid after chromatography on thin preparatory layer as described in EXAMPLE 12(a) is identical to the product prepared according to the EXAMPLE 12(a).

EXAMPLE 13

Preparation of potassium-6-phenoxyacetamidodehydropenicillanate (XXIV)

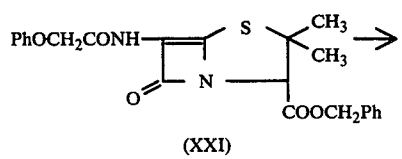

(XXI)

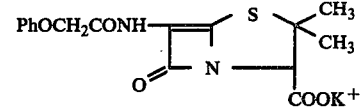

A solution in 20 mls of a mixture of ethanol-ethyl acetate (4:1) of 0.438 gram (1 millimol) of the product XXI prepared according to EXAMPLE 10, is hydrogenated in the presence of 0.430 gram of 10% palladium on activated char under atmospherical pressure and at room temperature for 30 mins. The catalyst is then filtered off and to the filtrate is added again 0.430 gram of fresh catalyst and the hydrogenolysis is continued during 40 additional minutes under the same conditions. The catalyst is filtered off again and the solution is immediately brought to a pH of 7.8–8.0 with a 5% aqueous solution of potassium bicarbonate and cooling with an ice bath. The mixture is evaporated to dryness in a vacuo at room temperature and the solid residue is taken up in ethyl acetate, filtered and the product XXIV is precipitated with ethyl ether from the solution. There is obtained 0.330 grams of XXIV (yield 85%).

IR (KBr) : $\nu$ max 3400 (wide band, (H$_2$O), 3320 (shoulder, NH), 3060 and 3040 (shoulder, phenyl), 1703 (CO of the beta-lactam), 1620 (CO of the phenoxyacetamide), 1602 (wide band, CO of the carboxylate), 1590 (shoulder, phenyl), 1555 (NH), 1493 cm$^{-1}$ (phenyl).

NMR (CD$_3$OD): δ 1.51 (3H,s) and 1.76 (3H,s) (CH$_3$)$_2$C, 4.38 (1H,s,3-4), 4.86 (2H,s,OCH$_2$CO), 6.85-7.40 (5H,m, aromatics).

The compound XXIV shows a light antibacterial activity with B. subtilis and Staph. aureus in the vitro dosage (agar plate diffusion test).

We claim:

1. 4-thioxo-2-azetidinone adapted to be cyclized to a 5,6-dehydropenicillin through treatment, in an anhydrous inert solvent, with an organic base or with a Bronsted or Lewis acid or with heat, and represented by the formula:

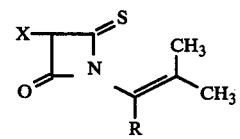

or

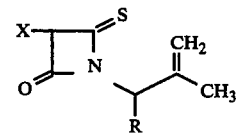

wherein X is a member of the group consisting of benzylamino, triphenylmethylamino, phenylacetamido, phenoxyacetamido and phthalimido, and R is a member of the group consisting of carboxyl, carboxylic salts, carboxylic amides, carboxylic esters and carboxylic thioesters.

2. 1-(1-methoxycarbonyl-2-methyl-1-propenyl)-3-phenoxy-acetamido-4-thioxo-2-azetidinone.

3. 1-(1-benzyloxycarbonyl-2-methyl-1-propenyl)-3-phenoxyacetamido-4-thioxo-2-azetidinone.

4. 1-(1-methoxycarbonyl-2-methyl-1-propenyl)-3-triphenyl-methylamino-4-thioxo-2-azetidinone.

5. 1-(1-methoxycarbonyl-2-methyl-1-propenyl)-3-acetamido-4-thioxo-2-azetidinone.

6. 1-(1-methoxycarbonyl-2-methyl-2-propenyl)-3-acetamido-4-thioxo-2-azetidinone.

* * * * *

UNITED STATES PATENT AND TRADEMARK OFFICE
CERTIFICATE OF CORRECTION

PATENT NO. : 4,133,807
DATED : January 9, 1979
INVENTOR(S) : Luciano Re, et al

It is certified that error appears in the above-identified patent and that said Letters Patent are hereby corrected as shown below:

Col. 2, line 4, Pattern I, Formula (III),

"$CH_3 + CH_3 COOR'$" should read --$CH_3 + CH_3 COR'$--.

line 10, Pattern I, Formula (IIa),

"CO—R'" should read --COR'--.

line 11, Pattern I, Formula (IIa),

"$CH_3$" should read --$CH_2$--.

Col. 4, Example 1, Formula (VII), Correct "$PH_3$" to read --$Ph_3$--.

Col. 6, line 2, Correct "$NH^+_3$" to read --$NH_3^+$--.

Col. 7, line 28, Correct "convention" to read --conventional--.

Signed and Sealed this

Tenth Day of July 1979

[SEAL]

Attest:

LUTRELLE F. PARKER
Attesting Officer    Acting Commissioner of Patents and Trademarks